United States Patent

Staggs

(10) Patent No.: US 8,366,728 B2
(45) Date of Patent: Feb. 5, 2013

(54) VACUUM SENSE CONTROL FOR PHACO PULSE SHAPING

(75) Inventor: James W Staggs, Laguna Niguel, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/473,959

(22) Filed: May 17, 2012

(65) Prior Publication Data

US 2012/0226221 A1 Sep. 6, 2012

Related U.S. Application Data

(63) Continuation of application No. 13/196,559, filed on Aug. 2, 2011, now Pat. No. 8,202,287, which is a continuation of application No. 12/684,657, filed on Jan. 8, 2010, now Pat. No. 7,998,156, which is a continuation of application No. 11/461,741, filed on Aug. 1, 2006, now Pat. No. 7,785,336.

(51) Int. Cl.
*A61B 17/32* (2006.01)
*A61B 17/20* (2006.01)

(52) U.S. Cl. .......................................... 606/169; 604/22

(58) Field of Classification Search .............. 606/107, 606/167, 169; 604/19, 22, 27, 28, 30, 93.01, 604/118
See application file for complete search history.

(56) References Cited

U.S. PATENT DOCUMENTS

| | | | |
|---|---|---|---|
| 2,434,480 A | 1/1948 | Anderson | |
| 3,857,387 A | 12/1974 | Shock | |
| 3,941,122 A | 3/1976 | Jones | |
| 4,184,510 A | 1/1980 | Murry et al. | |
| 4,343,111 A | 8/1982 | Inoue | |
| 4,736,130 A | 4/1988 | Puskas | |
| 4,808,948 A | 2/1989 | Patel et al. | |
| 4,827,911 A | 5/1989 | Broadwin et al. | |
| 4,952,834 A | 8/1990 | Okada | |
| 4,954,960 A | 9/1990 | Lo et al. | |
| 4,970,656 A | 11/1990 | Lo et al. | |
| 4,983,901 A | 1/1991 | Lehmer | |
| 5,001,649 A | 3/1991 | Lo et al. | |
| 5,091,656 A | 2/1992 | Gahn | |

(Continued)

FOREIGN PATENT DOCUMENTS

| | | |
|---|---|---|
| CA | 2242328 A1 | 5/1998 |
| DE | 19940712 A1 | 3/2001 |

(Continued)

OTHER PUBLICATIONS

Devine M.D., et al., "How to Set the Dials," Phacoemulsification Surgery, 1991, pp. 7-28.

(Continued)

*Primary Examiner* — Kevin C Sirmons
*Assistant Examiner* — William Carpenter
(74) *Attorney, Agent, or Firm* — Abbott Medical Optics Inc.

(57) ABSTRACT

A method and apparatus for precisely controlling particle movement relative to a phacoemulsification needle tip is provided. The design monitors actual vacuum present and calculates a pulse shape amplitude waveform proportional to the amount of measured vacuum. An increase in vacuum indicates that the handpiece/needle is becoming occluded by a large particle. The present design determines whether additional power is required to bump or move a large particle away from the needle tip. The present design may employ a control loop that senses and continuously monitors vacuum. The design may dynamically vary the amount of ultrasonic energy delivered to the surgical area in response to the observed actual vacuum, and can actively vary the amount of power delivered to the surgical area based on the size of the particle and the resultant vacuum realized.

7 Claims, 6 Drawing Sheets

U.S. PATENT DOCUMENTS

| | | |
|---|---|---|
| 5,209,221 A | 5/1993 | Riedlinger |
| 5,213,569 A | 5/1993 | Davis |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams, Jr. et al. |
| 5,417,246 A | 5/1995 | Perkins et al. |
| 5,431,664 A | 7/1995 | Ureche et al. |
| 5,453,087 A | 9/1995 | Malinowski |
| 5,520,633 A | 5/1996 | Costin |
| 5,534,741 A | 7/1996 | Smith |
| 5,547,459 A | 8/1996 | Kaufman et al. |
| 5,582,578 A | 12/1996 | Zhong et al. |
| 5,591,127 A | 1/1997 | Barwick, Jr. et al. |
| 5,700,240 A | 12/1997 | Barwick, Jr. et al. |
| 5,733,256 A | 3/1998 | Costin |
| 5,738,677 A | 4/1998 | Colvard et al. |
| 5,766,146 A | 6/1998 | Barwick, Jr. |
| 5,797,494 A | 8/1998 | Balling et al. |
| 5,800,365 A | 9/1998 | Zhong et al. |
| 5,808,396 A | 9/1998 | Boukhny |
| 5,836,959 A | 11/1998 | Seibel et al. |
| 5,852,794 A | 12/1998 | Staggs |
| 5,873,885 A | 2/1999 | Weidenbenner |
| 5,938,677 A | 8/1999 | Boukhny et al. |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,027,515 A | 2/2000 | Cimino |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 | 5/2002 | Cimino |
| 6,394,974 B1 | 5/2002 | Kadziauskas et al. |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,452,883 B2 | 9/2002 | Chan |
| 6,487,447 B1 | 11/2002 | Weimann et al. |
| 6,506,176 B1 | 1/2003 | Mittelstein et al. |
| 6,589,204 B1 | 7/2003 | Sussman et al. |
| 6,610,052 B2 | 8/2003 | Furumoto |
| 6,629,948 B2 | 10/2003 | Rockley et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 | 8/2004 | Kadziauskas et al. |
| 6,808,396 B2 | 10/2004 | Kawaguchi et al. |
| 6,884,252 B1 | 4/2005 | Urich et al. |
| 6,890,332 B2 | 5/2005 | Truckai et al. |
| 6,896,674 B1 | 5/2005 | Woloszko et al. |
| 6,908,472 B2 | 6/2005 | Wiener et al. |
| 6,939,317 B2 | 9/2005 | Zacharias |
| 6,962,583 B2 | 11/2005 | Kadziauskas et al. |
| 7,077,820 B1 | 7/2006 | Kadziauskas et al. |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 2001/0003155 A1 | 6/2001 | Rockley et al. |
| 2001/0003295 A1 | 6/2001 | Langlotz et al. |
| 2001/0003385 A1 | 6/2001 | Ise |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0073214 A1 | 3/2007 | Dacquay et al. |
| 2007/0078379 A1 | 4/2007 | Boukhny et al. |
| 2008/0146989 A1 | 6/2008 | Zacharias |

FOREIGN PATENT DOCUMENTS

| | | |
|---|---|---|
| EP | 270819 A2 | 6/1988 |
| EP | 270819 A3 | 1/1989 |
| EP | 336620 A2 | 10/1989 |
| EP | 336620 B1 | 12/1993 |
| EP | 1351631 A1 | 10/2003 |
| EP | 1537840 A1 | 6/2005 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A2 | 6/2001 |
| JP | 2002087836 A2 | 3/2002 |
| JP | 2002233534 A2 | 8/2002 |
| WO | WO9520374 A1 | 8/1995 |
| WO | WO9808442 A1 | 3/1998 |
| WO | WO0051508 A1 | 9/2000 |
| WO | WO0064388 A1 | 11/2000 |
| WO | WO0113838 A1 | 3/2001 |
| WO | WO02056806 A1 | 7/2002 |
| WO | WO2005092023 A2 | 10/2005 |

OTHER PUBLICATIONS

"Ocusystem Operation Manual, May 1995, 79 pages,".

"Pulsar cuts phaco time, boots efficiency in cataract removal; Ophthalmology Times: Aug. 15, 1986; 1 page, 11 (16), Harcourt Brace Jovanovich, Inc,".

Taylor W.F.,et al., "Intraoperative Troubleshooting of an Advanced Phacoemulsification System," The Surgial Technologist, 1985, vol. 17 (2), pp. 11-14.

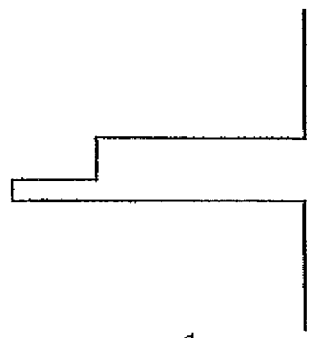
FIG. 5A
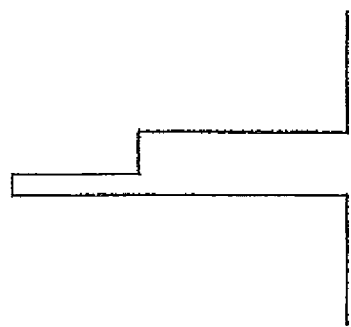
FIG. 5B
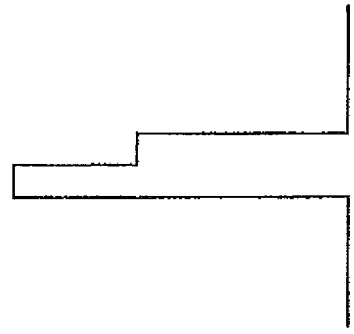
FIG. 5C
FIG. 5D
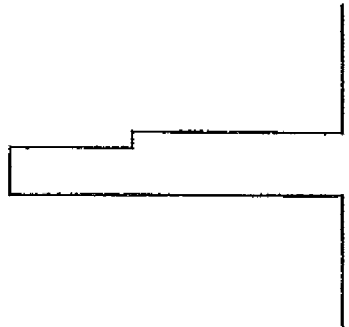
FIG. 5F
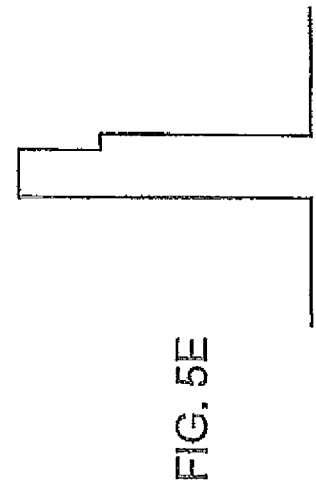
FIG. 5E

VACUUM SENSE CONTROL FOR PHACO PULSE SHAPING

This application is a continuation application of and claims priority to U.S. application Ser. No. 13/196,559 filed on Aug. 2, 2011, which is a continuation of U.S. application Ser. No. 12/684,657, filed on Jan. 8, 2010, now U.S. Pat. No. 7,998,156, that issued on Aug. 16, 2011, which is a continuation of U.S. application Ser. No. 11/461,741 filed on Aug. 1, 2006, now U.S. Pat. No. 7,785,336, that issued on Aug. 31, 2010 each of which is hereby incorporated by reference in its entirety.

BACKGROUND OF THE INVENTION

1. Field of the Invention

The present invention relates generally to the field of surgical tissue removal, and more specifically to ultrasonic power delivery during surgical tissue removal procedures such as phacoemulsification.

2. Description of the Related Art

Phacoemulsification surgery has been successfully employed in the treatment of certain ocular problems, such as cataracts. Phacoemulsification surgery utilizes a small corneal incision to insert the tip of at least one phacoemulsification handheld surgical implement, or handpiece. The handpiece includes a needle that is ultrasonically driven once placed within an incision to emulsify the eye lens, or break the cataract into small pieces. The broken cataract pieces may subsequently be removed using the same handpiece or another handpiece in a controlled manner. The surgeon may then insert lens implants in the eye through the incision. The incision is allowed to heal, and the results for the patient are typically significantly improved eyesight.

As may be appreciated, the flow of fluid to and from a patient through a fluid infusion or extraction system and power control of the phacoemulsification handpiece is critical to the procedure performed. Different medically recognized techniques have been utilized for the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens. Simultaneously with this emulsification, the handpiece provides a fluid for irrigation of the emulsified lens and a vacuum for aspiration of the emulsified lens and inserted fluids.

Pulse delivery has developed from a simple on/off arrangement through what is known as a burst delivery or pulse delivery, using fixed off periods or fixed duty cycles, to a specific pulse delivery such as the Whitestar pulse delivery method of Advanced Medical Optics Corporation of Santa Ana, Calif. Such designs provide the surgeon with different functionality useful in different phacoemulsification procedures, such as breaking the lens or removing the lens.

Previous systems have employed either an optimum phase angle to affect constant energy transfer into the tissue or apply a modulated voltage amplitude shaping pulse to control the phacoemulsification handpiece. These procedures can produce a significant amount of heat in the affected area. Care must be taken to avoid overheating of eye tissue during phacoemulsification while still performing the desired cutting or removal procedures. The risk of damaging the affected area via application of heat can be a considerable negative side effect.

Conditions may arise during ocular surgeries that reduce the cutting effectiveness of current pulse shaping designs. In particular, one undesirable effect exhibited by these systems is that small particles at the phaco tip can be knocked off from the tip at an undesirable time. The phaco tip must be sufficiently occluded by, or in contact with, the particle in order to effectively remove such particles. In order to circumvent or manage this effect, surgeons typically reduce the voltage amplitude shaping pulse to keep small particles from being knocked off at the tip. This method of reducing the voltage amplitude can materially limit cutting effectiveness. In general, blockage of the phaco tip dramatically reduces cutting effectiveness, as does any overall reduction in voltage amplitude applied.

Typical available systems may employ what is known as an occluded mode, wherein an occlusion or blockage of the phaco tip, such as by a piece of lens, is addressed in some manner. The typical way of addressing occlusion has been to cease operation until the tip is no longer occluded, i.e. simply releasing the pressure applied to the tip. This enables the operator/surgeon to manually move the tip and allow the occlusion to disengage from the instrument. such an implementation simply monitors the pressure of vacuum on the tip, and when it exceeds a certain amount, the vacuum is released or no longer applied.

Increased efficiency in this environment is desirable, such that any devices or procedures that can lessen heat applied to the affected area or simplify the work of the operator surgeon is beneficial. Patient recovery time can be enhanced when desirable performance is provided, such as reduced heat to the affected region.

Based on the foregoing, it would be advantageous to provide a system that employs a wave pulse shaping mechanism that enables successful surgeries without delivering excessive heat to the surgical site, and allows operators to operate the phacoemulsification system effectively under both occluded and non-occluded conditions. It would also be beneficial to overcome the aforementioned drawbacks present in previously known ultrasonic tissue removal systems.

SUMMARY OF THE INVENTION

According to one aspect of the present design, there is provided a method of delivering ultrasonic energy during a surgical procedure, such as a phacoemulsification procedure. The method comprises applying at least one pulse, and typically multiple pulses, each having a pulse shape. The pulse shape comprises a predetermined pulse shape portion and either an increased energy portion comprising an increase in energy proportional to an increase in sensed aspiration vacuum pressure or a decreased energy portion comprising a decrease in energy proportional to a decrease in sensed aspiration vacuum pressure.

According to a second aspect of the present design, there is provided an apparatus comprising a device configured to encounter vacuum pressure at the surgical area, a vacuum sensor configured to monitor vacuum pressure encountered by the device, and a computer configured to compute an ultrasonic pulse profile for delivery to a needle configured to vibrate based on the ultrasonic pulse profile received, the ultrasonic pulse profile based on monitored vacuum pressure received from the vacuum sensor. The ultrasonic pulse profile comprises a baseline ultrasonic pulse region and an altered ultrasonic pulse region, the altered ultrasonic pulse region comprising a pulse portion altered based on monitored vacuum pressure.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which:

FIGS. 5A-F show alternate examples of wave shapes according to the present design.

DETAILED DESCRIPTION OF THE INVENTION

Figure 1:
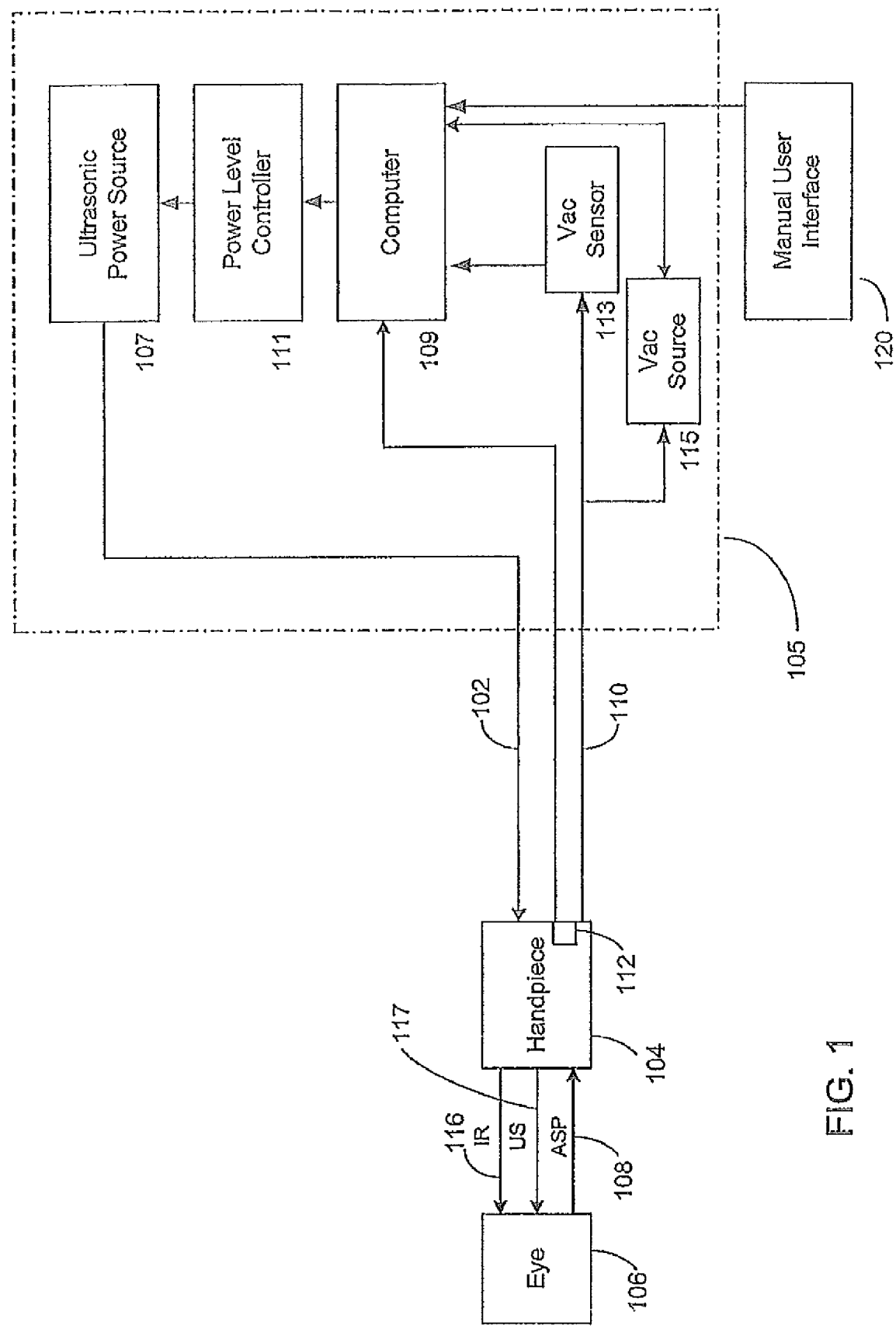
FIG. 1 is a functional block diagram of a phacoemulsification system in accordance with the present invention.

The following description and the drawings illustrate specific embodiments to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

Currently available phacoemulsification systems include a variable speed peristaltic pump, a vacuum sensor, an adjustable source of ultrasonic power, and a programmable microprocessor with operator-selected presets for controlling aspiration rate, vacuum and ultrasonic power levels. A phacoemulsification handpiece is interconnected with a control console by an electric cable for powering and controlling the piezoelectric transducer. Tubing provides irrigation fluid to the eye and enables withdrawal of aspiration fluid from an eye through the handpiece. The hollow needle of the handpiece may typically be driven or excited along its longitudinal axis by the piezoelectric effect in crystals created by an AC voltage applied thereto. The motion of the driven crystal is amplified by a mechanically resonant system within the handpiece such that the motion of the needle connected thereto is directly dependent upon the frequency at which the crystal is driven, with a maximum motion occurring at a resonant frequency. The resonant frequency is dependent in part upon the mass of the needle interconnected therewith, which is typically vibrated by the crystal.

One similar system and design is illustrated in U.S. patent application Ser. No. 10/387,335, entitled "Modulated Pulsed Ultrasonic Power Delivery System and Method," inventors Kenneth E. Kadziauskas et al., filed Mar. 12, 2003, the entirety of which is incorporated herein by reference.

Power control of the phacoemulsification handpiece is highly critical to successful phacoemulsification surgery. Certain previous systems address the requirements of power control for a phacoemulsification handpiece based on the phase angle between the voltage applied to a handpiece piezoelectric transducer and the current drawn by the piezoelectric transducer and/or the amplitude of power pulses provided to the handpiece. The typical arrangement is tuned for the particular handpiece, and power is applied in a continuous fashion or series of solid bursts subject to the control of the surgeon/operator. In certain circumstances, the surgeon/operator may wish to apply these power bursts for a duration of time, cease application of power, then reapply at this or another power setting. The frequency and duration of the burst is typically controllable, as is the length of the stream of bursts applied to the affected area. The time period where power is not applied enables cavitation in the affected area, and broken lens sections may be removed using aspiration provided by the handpiece or an aspiration apparatus. The on/off application of power facilitates breaking the cataract into pieces and relatively efficient removal thereof.

The present design provides a system and method for precisely controlling the movement of the phacoemulsification needle tip using a pulse shape controlled, or partially based on, sensed vacuum pressure. Controlling particle movement at the needle tip may enable better destruction (i.e. emulsification) of large and small particles. The present vacuum based design determines whether additional energy is required to bump or move a large particle away from the needle tip. The system may determine less energy is needed to enable a smaller particle to be drawn to the needle tip. The present design can include a control loop to sense and continuously monitor actual vacuum at the needle tip, and the design may vary the amount of ultrasonic power delivered to the surgical area in response to the observed actual needle tip vacuum. Moreover, the present design may actively vary the amount of ultrasonic power delivered based on the size of the particle, directly proportional to measured vacuum.

FIG. 1 illustrates a phacoemulsification system in block diagram form. The system has a control unit 105, indicated by the dashed lines in FIG. 1 that includes a source of pulsed ultrasonic power 107, a microprocessor computer 109 that provides control outputs to ultrasonic power level controller 111, and a vacuum source 115. A vacuum sensor 113 may continuously monitor and report the actual value of vacuum observed on line 110 and may provide these values for input to computer 109 representing the vacuum level, or actual vacuum level, received on the input side of vacuum source 115. Vacuum source 115 represents a vacuum source typically included within control unit or phacoemulsification device 105, generating a vacuum and attached to the line 110 and interfacing with computer 109 to provide actual vacuum pressure readings dynamically and receive signals to, for example, increase or decrease vacuum applied. Vacuum source may be provided separately from control unit 105.

The block representation of the handpiece 104 includes a needle and electrical means, typically a piezoelectric crystal, for ultrasonically vibrating the needle. The control unit 105 supplies power on line 102 to a phacoemulsification handpiece/needle 104. An irrigation fluid source is fluidly coupled to handpiece/needle 104 (not shown in FIG. 1). The irrigation fluid at 116 and ultrasonic power at 117 are applied by handpiece/needle 104 to a patient's eye, or affected area or region, indicated diagrammatically by block 106. Alternatively, the irrigation source may be routed to the eye 106 through a separate pathway independent of the handpiece. The eye 106 is aspirated by the using vacuum source 115 through line/handpiece needle 108 and line 110. Control unit 105 manages the amount of aspiration provided. A switch 112 disposed on the handpiece 104 may be utilized to enable a surgeon/operator to select an amplitude of electrical pulses to the handpiece via the computer 109, power level controller 111 and ultrasonic power source 107 as discussed herein. Any suitable input device such as, for example, a foot pedal (not shown) may be utilized in lieu of the switch 112.

The control unit 105 may include a manual user interface 120 to allow the surgeon/operator to preset various system parameters. User defined system parameters may include, but are not limited to, selecting pulse shape amplitude mode, setting maximum vacuum, minimum pulse shape amplitude, and maximum pulse shape amplitude. In addition, the computer 109 may provide operator-lettable limits for aspiration rates, vacuum levels and ultrasonic power levels. The surgeon/operator may select the pulse shape amplitude (PSA) mode during any phase of an operational procedure via the manual user interface 120 console. Selection of PSA mode may direct the microprocessor computer 109 to continuously monitor the resultant vacuum at line/handpiece needle 108 by measuring the pressure on line 110 via vacuum sensor 113. The computer 109 may respond to a surgeon selected preset maximum vacuum level and preset minimum and maximum PSA values using signals from the vacuum sensor 113. If the received vacuum from vacuum sensor 113 exceeds a maximum vacuum level as set by the surgeon, an occluded condition exists, and the system can halt vacuum pressure in an effort to enable occlusion removal.

Figure 2:
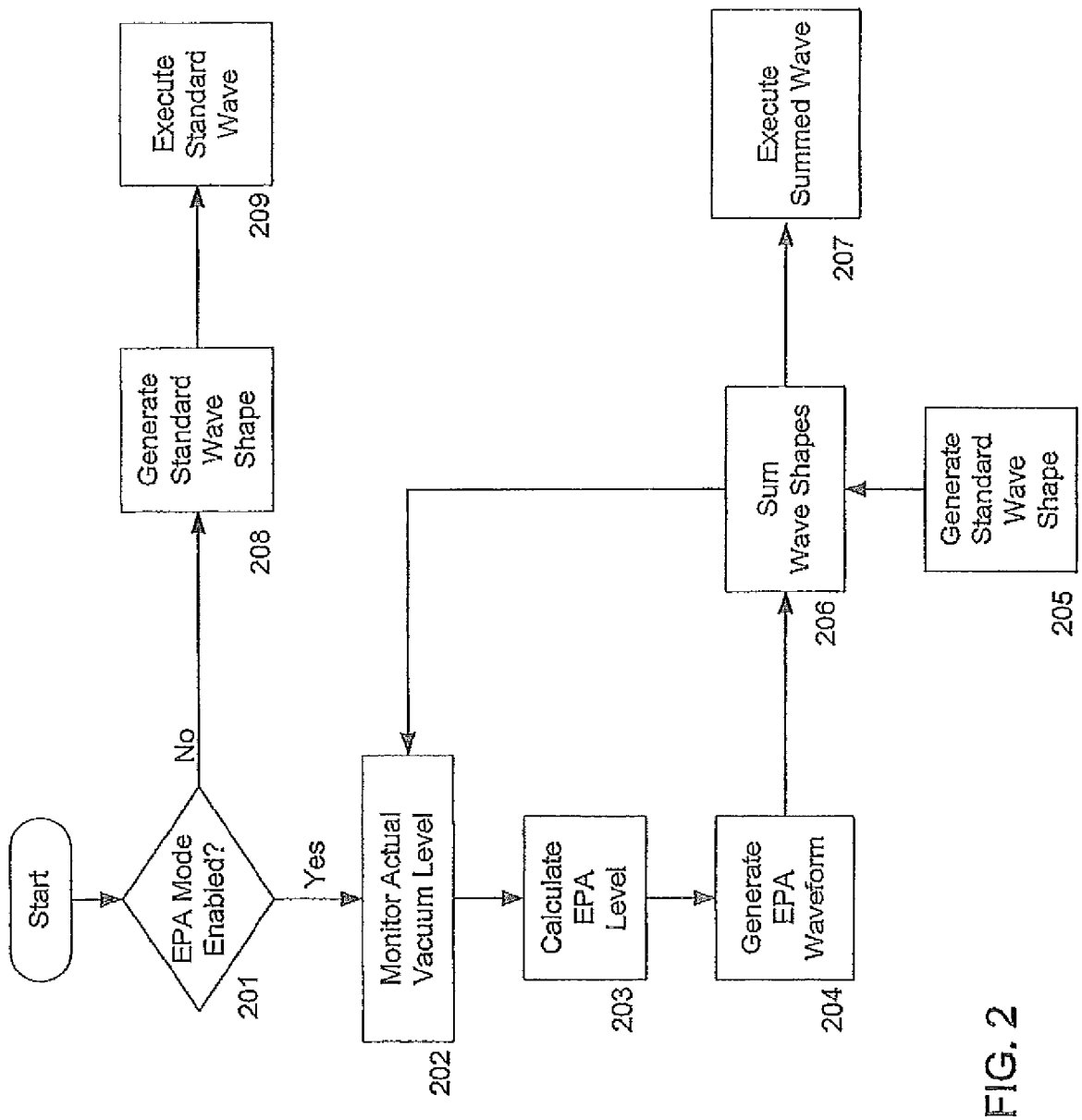
FIG. 2 is a flowchart illustrating the operation of a phacoemulsification system with variable ultrasonic power levels.

Operation of the control unit 105 in response to an occluded-unoccluded condition of handpiece 104 is shown in the flow diagram of FIG. 2. An occluded handpiece/needle 104 condition may arise when a large particle becomes held by vacuum at the handpiece/needle 104 tip. This situation is found to reduce the phacoemulsification cutting efficiency. Furthermore, large particles tend to be more readily emulsified when the particle is moved away from the handpiece/needle 104 tip. Conversely, an unoccluded handpiece/needle 104 may arise when a small particle is not held firmly in position and may fall off the handpiece/needle 104. In this situation, a reduction in ultrasonic power delivered may allow the smaller particle to be moved closer to the needle tip and may improve small particle destruction.

The present design may continuously vary the ultrasonic power delivered to the surgical area in response to particle size as determined by actual vacuum present on the aspiration line 108. Although the present design is described in terms of varying pulse shaping amplitude as a function of vacuum, alternate embodiments of the present design may include varying other system parameters such as phaco power and duty cycle as a function of vacuum, vacuum level, or vacuum pressure. Note that as used herein, the term "vacuum" is intended to mean any type of negative pressure, including a vacuum condition, vacuum level, or vacuum pressure.

As illustrated in FIG. 2, the surgeon/operator may enable PSA mode at point 201. The present design may continuously monitor actual vacuum level at point 202, where actual vacuum level represents the vacuum level present on line/handpiece needle 108 and line vacuum line 110. Microprocessor computer 109 may calculate a desired PSA level at point 203, where desired PSA level is typically a function of actual vacuum level, but may be a fixed value or function. The resulting PSA level obtained from this calculation may indicate to computer 109 a need to change the PSA level. Computer 109 may change the amount of ultrasonic energy delivered by supplying signals to power level controller 111 to generate an PSA wave shape at point 204 to increase, decrease, or maintain the amount of energy delivered. Power level controller 111 may superimpose the PSA wave shape at point 206 with the standard wave shape at point 205 resulting in an increase or decrease in ultrasonic power delivered based on actual vacuum level.

In this manner, the present design may dynamically change the total amount of energy delivered to the surgical area in real-time based on conditions encountered, specifically vacuum pressure received or sensed. The present design may provide a continuous control loop for increasing or decreasing the amount of ultrasonic energy delivered by performing an PSA wave shape function at point 207 based on the combination of the standard wave shape at point 205 modified by the PSA waveform at point 204 in response to measured vacuum. If the surgeon/operator elects to disable the PSA mode at point 201, the phacoemulsification system generates the standard phaco wave shape (e.g. burst, pulsed, etc.) at point 208 and performs the standard phaco wave shape at point 209.

The present design may calculate the pulse shape amplitude based on the following equation:

$$PSA = MinAmp + [(ActualVac)*(MaxAmp - MinAmp)]/(MaxVac) \quad (1)$$

where: MaxAmp=maximum pulse shape amplitude, MinAmp=minimum pulse shape amplitude, ActualVac=actual vacuum, MaxVac=maximum vacuum, and PSA=pulse shape amplitude.

Equation (1) provides valid pulse shape amplitude values for MaxVac values greater than zero. Table 1 provides resultant PSA values calculated based on an example of an implementation of Equation (1) using the following values:
MaxVac=200 mm/hg;
MinAmp=10%; and
MaxAmp=40%, where the percentage value represents percent above unmodified signal amplitude. 10% represents 10 percent above existing or nominal amplitude, or 110% of nominal.

TABLE 1

Example of Calculated PSA Versus Actual Vacuum

| ActualVac | PSA |
| --- | --- |
| 0 | 10% |
| 10 | 11.5% |
| 20 | 13% |
| 40 | 16% |
| 60 | 19% |
| 80 | 22% |
| 100 | 25% |
| 150 | 32.5% |
| 200 | 40% |

Figure 3:
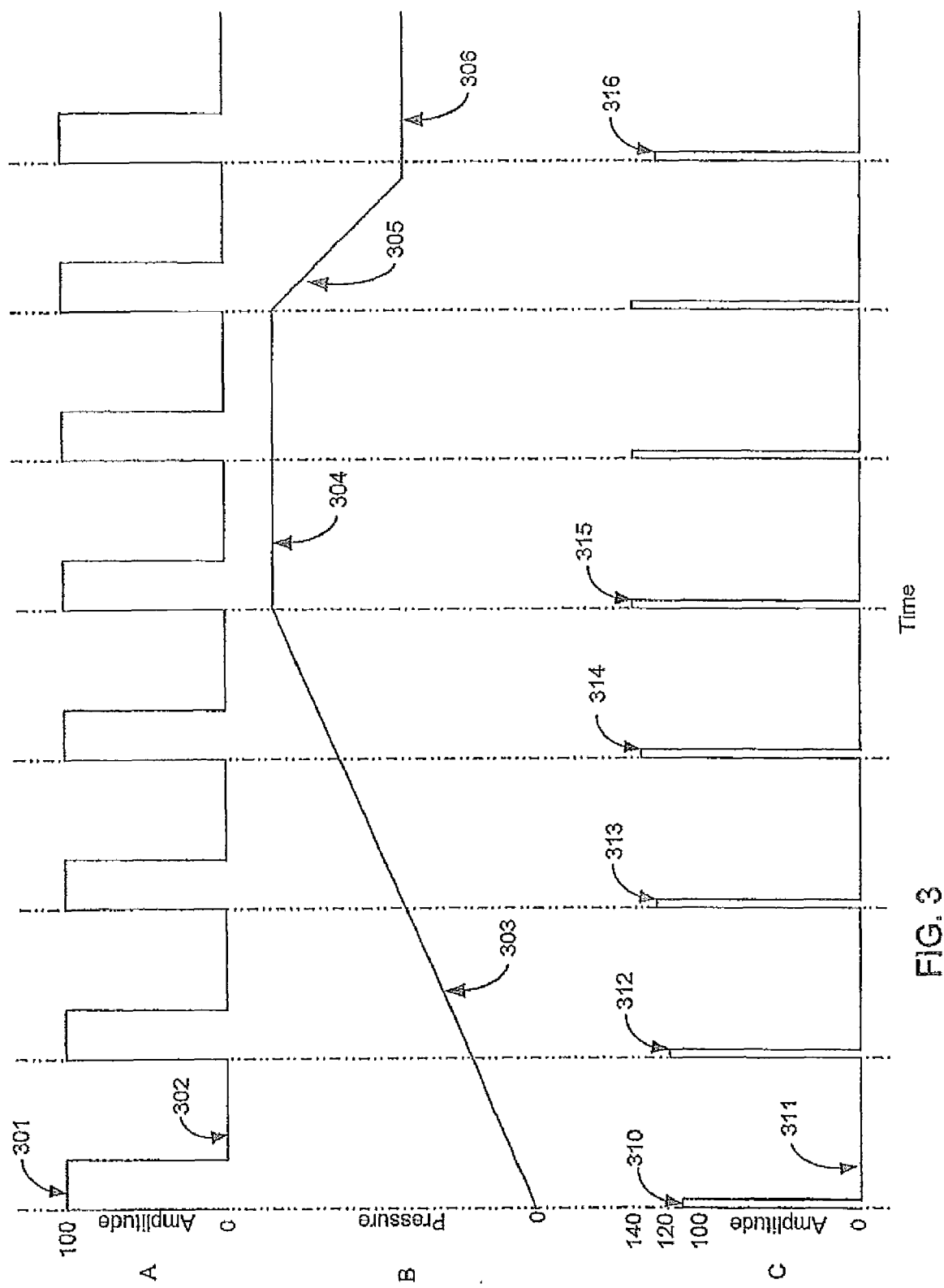
FIG. 3 illustrates a standard phacoemulsification ultrasonic wave shape, actual vacuum on aspiration line, and a calculated pulse shape amplitude waveform.

PSA is calculated as a percentage of the nominal wave amplitude generated by the phaco system. FIG. 3 illustrates the relationships between a standard phacoemulsification ultrasonic wave shape, actual vacuum measured on the aspiration line, and a calculated pulse shape amplitude waveform. Graph A in FIG. 3 represents an exemplary burst mode phaco wave shape with a duty cycle of 33%. The ultrasonic power on time is shown at point 301 with fixed amplitude. The ultrasonic power off time is shown at point 302. Although a phaco burst mode wave shape is shown, the present design may be applied to any standard or even non-standard phaco wave shape including a shape generated using pulse mode. Burst mode and pulse mode wave shapes known in the art. Graph B in FIG. 3 represents an example of actual vacuum measured on the aspiration line. In this example, the linear increase in vacuum pressure shown at point 303 may represent a larger particle beginning to occlude the phaco tip opening. Although the example is shown as having a linear increase in vacuum for simplicity, the present design may accommodate any dynamic changes in actual real-time vacuum. This occlusion may cause vacuum to build to a higher level as the phaco tip becomes more completely blocked off. The vacuum level at point 304 represents reaching the MaxVac as preset by the surgeon/operator in this example. This may represent a completely blocked off or occluded phaco needle tip.

The vacuum level at point 305 may represent a decrease in vacuum as the large particle is bumped or moved away from the phaco needle tip. Movement may result in a decrease in observed vacuum present of the aspiration line. The vacuum level at point 306 is representative of a large particle being precisely held away from the tip to ensure the most efficient destruction or emulsification of the large particle. The present design may generate the pulse shape amplitude waveform represented in Graph C in FIG. 3 based on the observed vacuum (Graph B) and the standard phaco wave shape either selected or provided (Graph A).

Based on the PSA equation, the present design may generate the pulse shape amplitude waveform with an ultrasonic on time at point 310 and off time at point 311. This generated PSA waveform amplitude is 10 percent greater than the standard wave shape shown in Graph A in accordance with a measured vacuum of 0 mm/hg. As vacuum pressure increases from 0 mm/hg to 200 mm/hg, the present design may generate the PSA waveforms shown at points 312, 313, 314 and 315. The PSA waveform increases proportionally to actual vacuum until the MaxVac value is reached.

In this example, the present design may generate a PSA waveform with amplitude 40 percent greater than the standard phaco wave shape shown in Graph A. The actual vacuum at point 304 may represent an occluded phaco needle tip. As the phaco power is increased via the PSA waveform augmentation to the standard or nominal waveform, the large particle may begin to move away from the needle and thus cause a drop in vacuum at point 305. As the large particle moves away from the Phaco needle tip, the needle tip may hold the large particle at a distance from the needle tip, enhancing emulsification of the particle. Large particle movement may be controlled or held in the present design by reducing the PSA waveform amplitude at point 316 in accordance with actual vacuum at point 306.

The amplitude of the wave generated may vary, but also the duration of the pulse and the additional amplitude spike may vary depending on circumstances. In general, a fairly short amplitude spike is added to the nominal waveform, where amplitude of the spike is dependent upon the calculation of Equation (1) or some similar vacuum based function.

Figure 4:
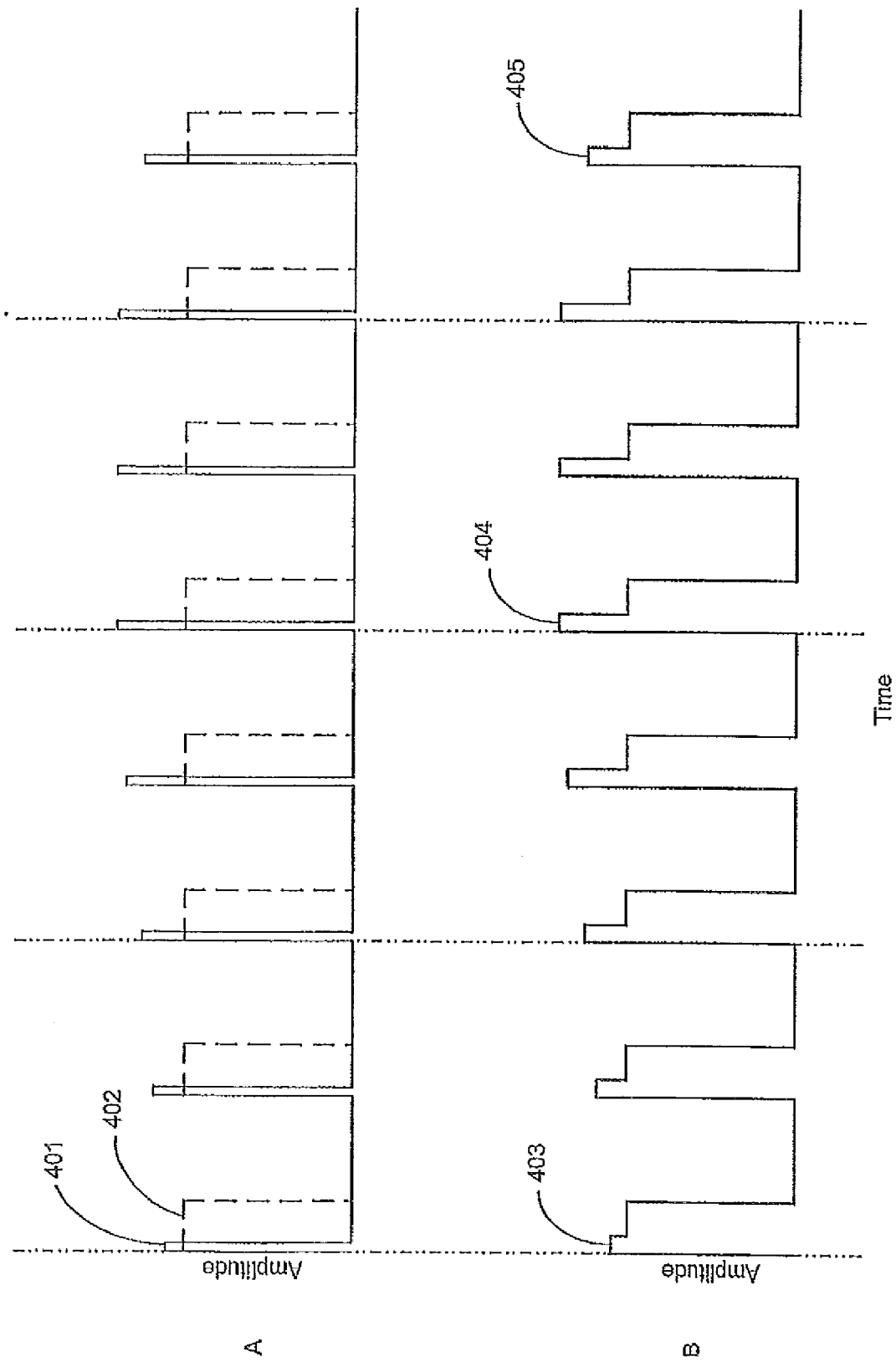
FIG. 4 illustrates a calculated pulse shape amplitude waveform superimposed on a standard phacoemulsification ultrasonic wave shape to produce a pulse shape amplitude wave shape.

FIG. 4 illustrates a calculated pulse shape amplitude waveform 401 superimposed on a standard phacoemulsification ultrasonic wave shape 402 in Graph A. The present design may combine or sum these two ultrasonic power signals to produce a modified ultrasonic wave shape for phacoemulsification as shown in Graph B of FIG. 4. This combination may form the pulse shape amplitude wave shape. Graph B represents a PSA wave shape in accordance with the vacuum profile shown in Graph B of FIG. 3. The ultrasonic profile represented at point 403 shows a 10% increase in amplitude generated by the present design for an actual vacuum of 0 mm/hg. The ultrasonic profile represented at point 404 shows a 40% increase in amplitude generated by the present design for an actual vacuum of 200 mm/hg. The ultrasonic profile represented at point 405 shows a 25% increase in amplitude generated by the present design for an actual vacuum of 100 mm/hg.

The ultrasonic power wave shape shown in Graph B of FIG. 4 represents an unoccluded condition at point 403, followed by an occluded condition at point 404 as a large particle is drawn closer and held at the phaco needle tip opening. Movement of the large particle away from the phaco needle tip occurs at point 405 due to the increased phaco power delivered at point 404. This increased power moves or bumps the large particle away from the phaco needle tip. In this automated configuration, the present design may enable the surgeon/operator to use less force to dissipate an occlusion by increasing the ultrasonic power as vacuum increases, thereby allowing the particle to be held firmly in position during emulsification. The present design may indicate to the surgeon the size of the particle by observing actual vacuum. In addition, the control loop mechanism within the present design may enable the surgeon to self-feed said particles at the phaco needle tip. The ability to self-feed large and small particles may eliminate the need for a second surgical instrument to push particles towards the phaco tip, as required by many currently deployed systems.

The present design has been described using an exemplary square wave phacoemulsification burst mode wave shape. As noted, although the description relates to how the present design modifies the amplitude of a standard pulse wave shape, the present design may alternately or additionally modify the width of the PSA waveform. In this arrangement, additional ultrasonic power may be delivered to the surgical area as required.

The illustrations presented in FIGS. 5A-5F illustrate pulses provided with enhanced amplitude that vary in duration, from a small percentage of the overall pulse width to a large percentage of pulse width. FIG. 5A illustrates one embodiment of a PSA wave shape. FIG. 5B illustrates a PSA wave shape with an increase in pulse shape amplitude over that shown in FIG. 5A. FIG. 5C illustrates an exemplary PSA wave shape wherein the width of the PSA waveform has been increased over that shown in FIG. 5A. Similarly, FIG. 5D illustrates an exemplary PSA wave shape wherein the width of the PSA waveform has been increased over that shown in FIG. 5B. FIG. 5E illustrates an exemplary PSA wave shape wherein the width of the PSA waveform has been increase over that shown in FIG. 5C, and FIG. 5F illustrates an exemplary PSA wave shape wherein the width of the PSA waveform has been increase over that shown in FIG. 5D.

The present design may modify amplitude and width of the PSA waveform in order to provide the desired ultrasonic power for efficient phacoemulsification of large and small particles.

Figure 6:
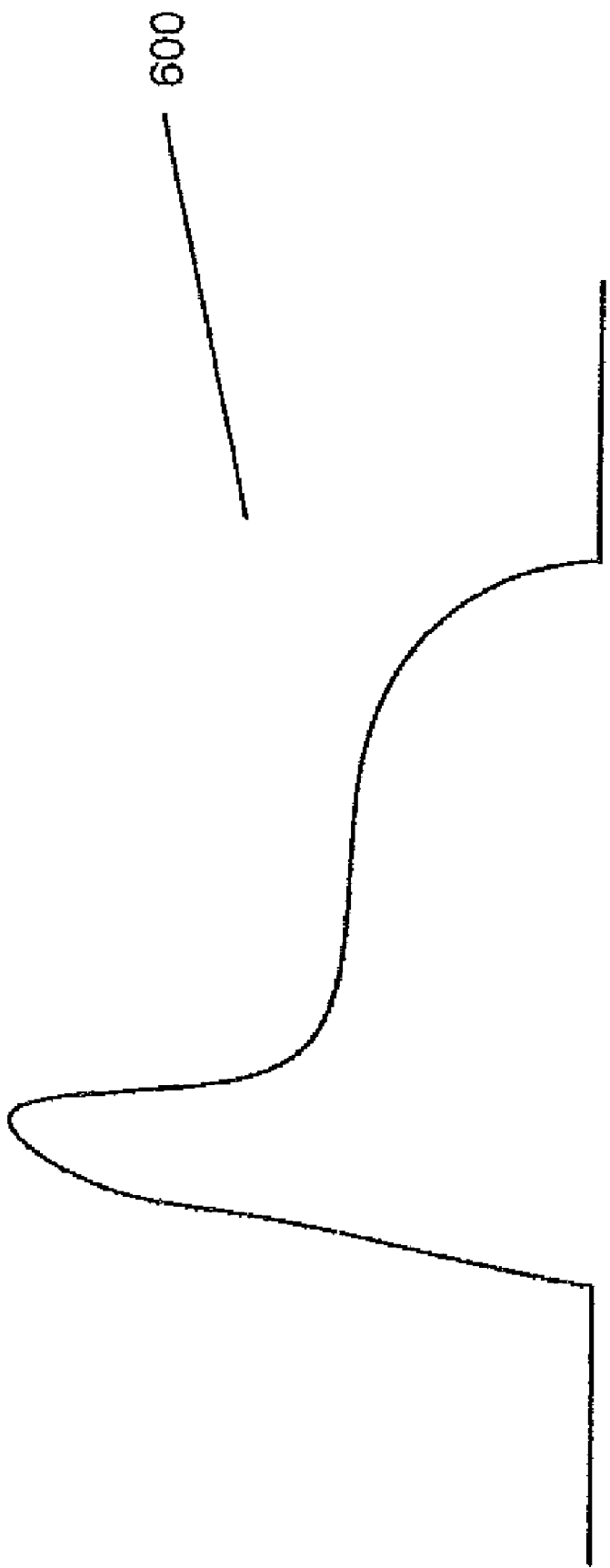
FIG. 6 shows an exemplary wave shape according to another embodiment of the present design.

The present design is not limited to generating square waves in response to the standard generated phaco wave shape. Other similar waveforms may be employed and depend on the environment encountered, including but not limited to phaco conditions, tip size, operating frequency, fluid conditions, and occlusion conditions. FIG. 6 illustrates an alternate aspect of the invention wherein rounded wave 600, or graduated power delivery curves are applied to the surgical area. In general, the rounded waveform follows the teachings presented herein, wherein pulse applied is based on vacuum pressure received and comprises a PSA enhanced amplitude region and a standard wave region. Other waveforms may be employed but are generally based in some form on vacuum pressure encountered.

A further aspect of the present design may include varying the time and power levels based on actual vacuum to attain transient cavatation as quickly as possible in the surgical environment without generating significant heat in the region. As may be appreciated by those skilled in the art, sufficient power is delivered based on the circumstances presented to induce transient cavatation, typically by delivering an initial higher power surge or burst of energy, followed by a drop off in energy from the initial surge in accordance with the present design.

Thus the present design delivers ultrasonic energy during a surgical procedure, such as a phacoemulsification procedure, and comprises applying at least one pulse and typically multiple pulses each having a pulse shape. The pulse shape comprises a predetermined pulse shape portion and either an increased energy portion comprising an increase in energy proportional to an increase in sensed aspiration vacuum pressure or a decreased energy portion comprising a decrease in energy proportional to a decrease in sensed aspiration vacuum pressure. Alternately, the design monitors actual vacuum pressure level at the surgical region, dynamically calculates a pulse shape amplitude (PSA) level based on monitored actual vacuum pressure level, generates a PSA waveform based on the dynamically calculating, and sums a predetermined wave shape with the PSA waveform to produce a PSA wave shape. The design then delivers the PSA wave shape to a handpiece.

The design may be embodied in an apparatus comprising a device configured to encounter vacuum pressure at the surgical area, a vacuum sensor configured to monitor vacuum pressure encountered by the device, and a computer configured to compute an ultrasonic pulse profile for delivery to a needle configured to vibrate based on the ultrasonic pulse profile received, the ultrasonic pulse profile based on monitored vacuum pressure received from the vacuum sensor. The ultrasonic pulse profile comprises a baseline ultrasonic pulse region and an altered ultrasonic pulse region, the altered ultrasonic pulse region comprising a pulse portion altered based on monitored vacuum pressure.

As may be appreciated by those skilled in the art, the present design may be realized in software executing in microprocessor computer 109, or may be implemented with dedicated microcontrollers or analog circuitry.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a method of generating a pulse shape amplitude in an arrangement that modifies phaco ultrasonic power delivered proportional to actual vacuum present. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for applying ultrasonic energy to a device used in a surgical region, comprising:
    monitoring actual vacuum pressure level at the surgical region;
    dynamically calculating a pulse shape amplitude (PSA) level based on monitored actual vacuum pressure level;
    generating a PSA waveform based on said dynamically calculating;
    summing a predetermined wave shape with the PSA waveform to produce a PSA wave shape; and
    delivering said PSA wave shape to a handpiece.

2. The method of claim 1, wherein said monitoring actual vacuum pressure level occurs using a device separate from the handpiece.

3. The method of claim 1, wherein said handpiece comprises a needle that vibrates based on the PSA wave shape received from said delivering.

4. The method of claim 1, wherein dynamically calculating comprises assessing based on actual sensed aspiration vacuum pressure multiplied by maximum pulse amplitude minus minimum pulse amplitude and divided by maximum sensed aspiration vacuum pressure; added to minimum pulse amplitude.

5. The method of claim 1, wherein the delivering tends to induce transient cavitation within the surgical region.

6. The method of claim 1, wherein monitoring actual pressure level occurs using a first aspiration device.

7. The method of claim 1, wherein said dynamically calculating, generating, summing, and delivering is repeated, thereby delivering multiple pulses each comprising an individual pulse shape formed based on actual sensed aspiration vacuum pressure.

\* \* \* \* \*